United States Patent [19]

Treiber et al.

[11] 4,198,338

[45] Apr. 15, 1980

[54] PROCESS FOR PURIFYING THIENAMYCIN

[75] Inventors: Laszlo R. Treiber, Gillette; Vincent P. Gullo, Edison, both of N.J.

[73] Assignee: Merck & Co., Inc., Rahway, N.J.

[21] Appl. No.: 885,836

[22] Filed: Mar. 13, 1978

[51] Int. Cl.$^2$ .................... C07D 489/04; A61K 31/40
[52] U.S. Cl. .................. 260/326.31; 424/123; 424/124; 424/274; 204/158 R; 435/47
[58] Field of Search .................. 260/326.31; 424/123, 424/124

[56] References Cited

U.S. PATENT DOCUMENTS

| | | | |
|---|---|---|---|
| 3,950,357 | 4/1976 | Kahan et al. | 260/326.31 |
| 4,000,161 | 12/1976 | Geogelman et al. | 260/326.31 |

*Primary Examiner*—Mary C. Lee
*Attorney, Agent, or Firm*—Hesna J. Pfeiffer; Julian S. Levitt

[57] ABSTRACT

Fermentation broths or impure solutions containing thienamycin, a substance having antibiotic activity against gram-negative and gram-positive microorganisms, are purified using a sequence of ion exchange resins, starting with an anion exchange resin of the polystyrene-trimethylammonium type in the $HCO_3$-cycle, and ending with absorption on and elution from a polymeric cross-linked polystyrene-type resin adsorbent. Variations in the intermediate steps, e.g. different resins and eluates are possible and are illustrated within.

2 Claims, No Drawings

PROCESS FOR PURIFYING THIENAMYCIN

BACKGROUND OF THE INVENTION

The antibiotic, thienamycin, is obtained by growing strains of a particular microorganism in suitable aqueous nutrient media under controlled conditions. It can be purified as described in U.S. Pat. No. 4,000,161, issued Dec. 28, 1976. This invention is directed to an improved method for recovering this antibiotic in substantially pure, stable form in higher yields than that of the prior art.

SUMMARY OF THE INVENTION

This invention relates to methods for recovering and purifying the novel antibiotic compound, thienamycin, having the following structural formula:

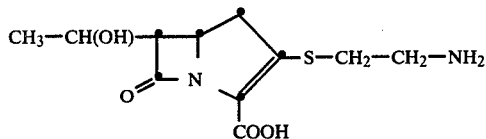

from fermentation broths in which the antibiotic is produced or from solutions containing partially purified antibiotic. This is achieved by contacting the fermentation broth in which the antibiotic is produced or a solution of partially purified antibiotic with a polystyrene-type anion exchange resin the preferred eluant depending on the type of resin used, followed by chromatography on an adsorbant such as polystyrene, hydrophobic cross-linked divinyl benzene polymers.

Thienamycin is effective in inhibiting the growth of various gram-negative and gram-positive microorganisms.

DESCRIPTION OF THE PREFERRED EMBODIMENTS

Thienamycin is produced during the aerobic fermentation of suitable aqueous nutrient media, under controlled conditions, by a strain of *Streptomyces cattleya* capable of producing said compound, for instance by the strain on permanent deposit in the culture collection of the Northern Utilization Research and Development Branch of the U.S. Department of Agriculture at Peoria, Ill. under accession number NRRL 8057. Its growth requirements, characteristics, as well as properties of the product and dosage forms, etc., are disclosed in U.S. Pat. No. 3,950,357, issued Apr. 13, 1976.

The antibiotic containing fermentation broths produced in accordance with the procedures described in the latter patent have activities ranging from about 50 to 400 units per ml. when assayed in accordance with the disc-diffusion assay using *Staphylococcus aureus* ATCC 6538P. Antibiotic preparations having at least 2 units of activity per mg. of broth solids, can be purified and the antibiotic rcovered by a number of processes.

One such procedure comprises adsorbing thienamycin on an anion exchange resin of the crosslinked polystyrene-trimethylammonium type on the $HCO_3^-$ cycle and eluting with water saturated with $CO_2$. The eluate so obtained can be further purified by the following processes:
repeat ion exchange chromatography on an anion exchange resin of the cross-linked polystyrene-quaternary ammonium type; chromatography on an anion exchange resin with a buffer or water; and chromatography on an adsorbing resin of the cross-linked polystyrene type.

The sequence in which the processes are carried out is not critical, nor are all intermediate process steps necessary. Additional intermediate steps can be used, such as a chromatography on a cation exchange resin and/or passage through a gel filtration resin. It is preferred to use the sequence wherein the ion exchange resin purification is used for the more impure broths and solutions and the polymeric adsorbing resin steps are used for material which has already been at least partially purified.

Examples of preferred sequences of steps for recovering the antibiotic thienamycin from fermentation broths or from solutions containing the antibiotic comprises passing a fermentation broth or a solution containing the antibiotic through a column packed with an anion exchange resin of the cross-linked polystyrene-quaternary ammonium type on the $HCO_3^-$ cycle; collecting the effluent; optionally repeating the first step; concentrating the eluate; passing the effluent through a column packed with a similar type of anion exchange resin; concentrating the effluent; adsorbing the concentrated effluent on a column packed with a polystyrene, hydrophobic cross-linked divinyl benzene polymer; eluting the polymer with water or a phosphate buffer; collecting the eluate and combining the active fractions, and in the case of phosphate buffer eluate, repeating the last step of adsorption and elution from the divinyl benzene polymer using water as the eluate. Another sequence of steps comprises, after the first $HCO_3^-$ resin step, then passing the solution through a column packed with a cation exchange resin containing sulfonic acid exchange groups; eluting the resin adsorbate with water or a weak base; collecting the eluates; and then passing into an anion exchange resin containing quaternary ammonium exchange groups. Another sequence employs a step involving passage through a gel filtration resin such as a polyacrylamide or dextran gel, instead of the anion resin step.

In the above description, the following resins are commercial examples of the illustrative examples. Those of the sulfonate type having a styrene-divinyl benzene matrix include the polystyrene nuclear sulfonic acid resin Dowex 50×2 (manufactured by Dow Chemical Co., Midland, Mich.), on the sodium cycle. Other representative members of the class of strong cation exchange resins include the following: Dowex 50×4, Dowex 50×8, (manufactured by Dow Chemical Co., Midland, Mich.), Amberlite IR120 (manufactured by Rohm & Haas Co., Philadephia, Pa.), Duolite C25D (manufactured by Chemical Process Co., Redwood City, Calif.), Permutit Q (manufactured by Permutit Co., Birmingham, N.J.), Ionac C-249 (manufactured by Ionac Chemical Co., Birmingham, N.J.) and Amberlite 200.

The gel filtration resin can be a polyacrylamide or dextran gel. Generally, a gel of 50–100 mesh which will allow the fractionation and desalting of substances with molecular weights from 200–2000 is used. Gels of 50∝400 mesh may also be employed, the particular mesh employed depending upon the size of the column to be used. Examples of suitable gels are dextran cross-linked with epichlorhydrin and available in bead form as Sephadex G-10 from the Pharmacia Company, Sweden which excludes molecules having a molecular weight greater than 700, and polyacrylamides crosslinked with methylene bisacrylamide available in bead form as Bio-Gel P-2 from Bio-Rad Laboratories, Richmond, Calf., which excludes molecules having a molecular weight greater than 1800. The pH of the antibiotic solution to be purified is preferably adjusted to about neutral, and the solution contacted and equilibrated with the gel. The antibiotic is then removed from the gel with water or another suitable eluting agent such as an aqueous solution of a lower alcohol, or buffer. The eluate is collected in fractions and those determined to be most active by bioassay are combined.

Elution from the cation exchange resin can be accomplished with aqueous solutions of organic bases such as pyridine; $\alpha$, $\beta$, or $\gamma$picoline; 2,3-, 2,4- and 2,6-lutidine; 2,4,6-collidine and alkyl amines wherein the alkyl groups containing 2 to 10 carbon atoms. The preferred base for eluting the cation exchange resin is pyridine.

Illustrative anion exchange resins of the polystyrene-trimethylammonium type are Dowex 1×2 or Dowex 1×4 in the chloride or $HCO_3^-$ cycle. Other suitable examples are Dowex 1×8, Dowex 21K, Dowex SBP-R, Amberlite IRA-401 S, Amberlite IRA-400 or Amberlite IRA-401. A suitable polymeric adsorbent is e.g., XAD-2, a polystyrene resin or other similar commercially available materials, such as Duolite ES-863.

The examples which follow illustrate the methods by which the products of this invention may be obtained. However, the examples are illustrative only and it should be apparent to one having ordinary skill in the art that this invention includes the functionally equivalent products and methods for their preparation. Therefore, any modification of the processes described herein which results in the formation of an identical product should be construed as constituting an analogous method. The described processes are capable of wide variation and modification and any minor departure or extension is considered as being within the skill of the artisan and as falling within the scope of this invention. Bioactivity of eluates is measured by assaying the eluate using *Staphylococcus aureus* ATCC 6538P as the assay organism, using the following procedure.

ASSAY

Assays of antibacterial activity are run according to the following disc-diffusion procedure unless otherwise indicated. The assay plates are prepared in the following manner. An overnight growth of the assay organism, *Staphylococcus aureus* ATCC 6538P, in nutrient broth plus 0.2% yeast extract is diluted with nutrient broth plus 0.2% yeast extract to a suspension having 55% transmittance at a wavelength of 660 m$\mu$. This suspension is added to Difco nutrient agar supplemented with 2.0 g/l/Difco yeast extract, at 47° C. to 48° C., to make a composition containing 32.2 ml of the suspension per liter of agar. Five ml. aliquots of this suspension is poured into petri dishes at 85 mm. diameter, and these plates are chilled and held at 4° C. until used (5 day maximum).

Samples of the antibiotic to be assayed are diluted to an appropriate concentration in phosphate buffer at pH 7. Filter-paper discs, 0.5-inch in diameter, are dipped into the test solution and placed on the surface of the assay plate; two discs for each sample are normally placed on one plate opposite to one another. The plates are incubated overnight at 37° C. and the zone of inhibition is measured as mm diameter. The zone of inhibition measured in mm determines relative potencies or, when compared with a purified reference standard such as cephalothin, the potency or antibiotic in units/ml. One unit is defined as the amount which calculates to produce the same inhibition as 1 $\mu$g cephalothin/ml, that zone of inhibition being between 16 and 21 mm diameter.

The thienamycin concentration of the solution is determined by either high pressure liquid chromatography (HPLC) or photometry at 297 mn. Background correction is accomplished in both cases by treatment of the samples with hydroxylamine.

HPLC: The separation is carried out on a Bondapak $C_{18}$ column (Waters Associates, Inc., Mildford, Mass. 01757).

Mobile Phase: 0.01 M $KH_2PO_4$.

Temperature: 38° C.

Appropriate dilutions of the samples are made as to have a maximum amount of 2.5 $\mu$g per injection. The elution is monitored by means of a UV detector adjusted to 297 mn. The quantitative evaluation of the chromatograms is based on comparison with a standard solution of known concentration.

Photometry: UV absorption of the sample is compared with the same of a standard of 25 $\mu$g/ml at 297 mn. Then both the sample and standard are treated with the same amount of hydroxylamine at room temperature until a stable UV reading is obtained. The concentration of the sample is calculated from the UV absorbance units extinguished by hydroxylamine. The standard gives the extinguishable absorbance units per $\mu$g of thienamycin.

EXAMPLE 1

The pH of 55 l of filtered broth was adjusted to 7.2 (from 6.9). The cold broth was fed onto a precooled Dowex 1×4 column (5 l, 10 cm i.d., mesh 50–100) in the $HCO_3^-$ cycle. The loaded resin was washed with cold distilled water. Both feeding and washing were conducted at a flow rate of 1.0 l/min. 55 l of broth containing 598 mg of thienamycin were loaded onto the column. It was eluted with $CO_2$-saturated water at a flow rate of 0.3 l/min. 55 l of spent, 6 l of wash and 5.48 l of forecut contained together 25.4 mg (4.25%) of thienamycin. In 8.15 l of rich cut 477 mg (79.9%) of thienamycin were recovered. Purity: 5.50%. The material balance is complete with 10 mg (1.68%) of thienamycin in 2.75 l of tail cut. The rich cut was concentrated by vacuum distillation to 52 ml where 376 mg (78.8%) of thienamycin have been recovered.

The above concentrate was loaded onto a Dowex 50×2 column (1 l, 5.0 cm i.d., mesh 50–100) in the Na+ cycle. It was eluted with cold water at a flow rate of 30 ml/min. The volume of each fraction was approximately 235 ml. The fractions Nos. 6–14 were combined to constitute the rich cut in a yield of 38.1% (corresponding to 143 mg of thienamycin in 2096 ml). Purity: 12.7%. The sample was concentrated again in vacuo, in 95% yield, to 9.5 ml.

The concentrate was applied onto a Bio-Gel P-2 column from Bio-Rad Laboratories, Richmond, Calif. (200 ml, 3.0 cm i.d., mesh 200–400) and eluted with cold distilled water. Flow rate: 2.8 ml/min. 5.4 ml samples were collected after the void volume. Eluates Nos. 4–8 were combined. In 26.8 ml solution 91.0 mg of thienamycin was obtained corresponding to a yield of 67.4%. Purity: 42%. The volume of the rich cut was reduced by vacuum distillation to 6.8 ml. The recovery of the concentration was 83%.

The above concentrate containing 57.9 mg of thienamycin was applied onto an XAD-2 column (67 ml, 1.6 cm i.d., mesh 20-50) and eluted with cold distilled water at a flow rate of 2 ml/min. After the collection of six forecuts totaling 65 ml, 17 ca. 7 ml samples were collected. Fractions Nos. 7-17 contained the rich cuts and Nos. 18-23 the tail. In the composite rich cut of 77.4 ml, 43.4 mg of pure thienamycin were obtained. Yield: 74.7%. With respect to the small amount, no attempt was made to freeze-dry the product.

The overall yield was calculated 9.52%.

The temperature was kept throughout the procedure at 5° C. The pH of the thienamycin solutions was maintained between 6-7. The thienamycin assays were carried out by HPLC.

EXAMPLE 2

The pH of the filtered broth was adjusted to 7.27 with $NH_4OH$ (from 6.78). The cold broth was fed onto a precooled Dowex 1×4 column (5 l, 10 cm i.d., mesh 50-100) in the $HCO_3^-$ cycle. The loaded resin was washed with cold distilled water. Both feeding and washing were conducted at a flow rate of 1.2 l min. 45 l of broth containing 691 mg of thienamycin were loaded onto the column. It was eluted with $CO_2$-saturated water at a flow rate of 0.3 l/min. 45 l of spent, 6 l of wash and 6 l of forecut were collected. In these cuts 98.5 mg (14.3%) of thienamycin were recovered. 9.69 l of rich cut contained 593 mg (85.9%) of thienamycin. Purity: 5.11%. All the assays were carried out by HPLC.

The pH of the eluate was adjusted to 4.10 at 5° C., and was used as feed for a Dowex 50×2 column (650 ml, 5.5 cm i.d., mesh 50-100) in the $NH_4^+$ cycle. Flow rate: 240 ml/min. during the loading, and washing with distilled water. In the spent (9.69 l), was (650 ml) and forecut (519 ml) 99.7 mg (16.6%) of thienamycin were recovered. The elution was carried out with 2% aq. pyridine to provide 229 mg (49.8% yield) thienamycin in 736 ml. The purity of the product was 14.8%. Pyridine was immediately removed by vacuum distillation. The remaining residue (ca 380 ml) was stabilized by adjusting the pH to 6.7 (from 7.8) by adding some $CO_2$ to it. The sample was stored overnight at 5° C. Next day, the sample was concentrated to 39 ml. The recovery of storage and volume reduction was 267 mg (89%).

The concentrate was loaded onto a Dowex 1×2 column in the $CL^-$ cycle (500 ml 2.8 cm i.d., mesh 50-100), and eluted with cold distilled water at a flow rate of 10 ml/min. The volume of the first fraction was 191 ml. The subsequent fractions were about 50 ml. The rich cuts (El. Nos. 7-12) were combined. The sample of 299 ml contained 234 mg (yield 87.6%) of thienamycin. The forecut (Nos. 1-6) tailcut (Nos. 13-14) contained an additional amount of 17 mg (6.4%). The purity of the product was 64.5%. About 10% of the sample was used for assays. The remaining solution was concentrated to 30.5 ml in a recovery of 95.4%. 199 mg of thienamycin were thus loaded onto a precooled XAD-2 column (450 ml, 2.8 cm i.d., mesh 20-50), and eluted with cold distilled water at a flow rate of 10 ml/min. About 580 ml of eluate were collected as forecut, 634 ml as rich cut and 158 ml of tailcut. The rich cut contained 164 mg (82.7% yield) of thienamycin the purity of which was 90%. In the fore- and tailcut, 25 mg of thienamycin were recovered (12.6%). The rich cut was concentrated by vacuum distillation to 110 ml and freeze-dried. The thienamycin content of the freeze-dried material was 84.4%.

The overall yield amounted to about 19.8%.

The thienamycin samples were kept cold (about 5° C.) and the pH was adjusted to the range of 6-7.

EXAMPLE 3

A 5110 l fermentation broth was neutralized, cooled and filtered to give 4769 l filtered broth. The HPLC assay gave 12.7 mg/ml (60.4 g total). In order to correct for the baseline, an $NH_2OH$-treated sample was also assayed. The pH was 7.07.

The cold filtered broth was fed simultaneously onto two Dowex 1×2 columns (mesh 50-100) in $HCO_3^-$ cycle (416 l, 75 cm i.d. each, precooled). Flow rate: ca. 34 l/min on each column. The loaded columns were washed with cold deionized water and then eluted with cold water saturated with $CO_2$. The elution was monitored by spectrophotometry at 297 nm. The fractions were analyzed by HPLC. The spent, wash and forecut contained no measurable amount of thienamycin. The recovery in the rich cut was virtually quantitative: 64.7 g, 107% in 1249 l sample. Purity: 6.5%. $CO_2$ was removed from the eluate in vacuo. The residue, 1185 l of solution, containing 60.7 g thienamycin (quantitative recovery), was used for the following step, which was in essence the repetition of the previous procedure.

An 83.3 l, 35 cm i.d., Dowex 1×2 column (mesh 50-100) in the $HCO_3^-$ cycle was cooled by washing with cold deionized water. The pH of the eluate of the previous Dowex 1×2 step was adjusted to 8.04. The solution was then fed to the column at a flow rate of 4.7 l/min. The loaded column was washed with cold deionized water, and eluted with cold, $CO_2$ saturated, deionized water. No thienamycin was detected in the spent, wash and forecut. The rich cut, 189.3 l, contained 46.7 g of thienamycin corresponding to a yield of 77.6% for this particular step. Purity: 10.4%. An additional amount of 1.21 g (2.01%) was recovered in the tail cut, but only the rich cut was used for the next step. It was concentrated by reverse osmosis first to about 57 l, then by vacuum distillation. The 6.4 l concentrate contained 36.9 g of thienamycin (77% yield).

The concentrate was loaded onto a Dowex 1×2 column (mesh 50-100, 83.3 l, 35 cm i.d.) in $Cl^-$ cycle. The column was eluted with cold deionized water at a flow rate of about 2 l/min. After approximately 60 l as forecut, 12 samples of 8 l each were collected. El. Nos. 13-19 were 18.9 l each. The fractions were analyzed by HPLC for concentration. Based on purity assays eluates Nos. 16-19 were combined to constitute the rich cut of 188 l containing 28.7 g of thienamycin (77.6% yield). The purity was 39.6%. Additional cuts containing 3 g of thienamycin were not used because of insufficient purity (20%). The rich cut was concentrated by reverse osmosis and vacuum distillation from 152 mg/l to 4594 mg/l in 89.9% yield. The final concentrate, 5.6 l contained 25.7 g of thienamycin, purity: 37%.

The above concentrate was loaded onto an XAD-2 column (83.3 l, 35 cm i.d., mesh 20-50) prepared as follows: The resin was washed within a sequence with 2 column volumes of 60% aq. acetone and with deionized water acetone free. Just before being used, it was washed again with cold deionized water.

The column was eluted with cold deionized water at a flow rate of about 2 l/min. The volume of the first cut was 83.3 l, all the following fractions were 12 l. Based on the HPLC assay and purity data, El. Nos. 3-10 were combined. In the 84 l sample 17.1 g of thienamycin were found, corresponding to 66.6% yield. The other fractions contained additionally 8.3 g thienamycin (32.2%). The composite rich cut was concentrated in vacuo in three portions at pH 7.8, 6.8 and 6.4. The concentrations were 1.83 g/l, 2.46 g/l and 2.45 g/l, respectively. The samples were freeze-dried. Assay by HPLC gave the following thienamycin content: 54.8%, 65.6%, and 62.5%, respectively. Samples were submitted for the determination of sulfated ash. 31.9% sulfated ash indicated high content of inorganic materials introduced by the low quality deionized water. The total thienamycin content was 15.7 g corresponding to an overall yield of approximately 26%.

EXAMPLE 4

A 4069 l fermentation broth was neutralized and assayed by HPLC. Titer 19.8 $\mu$g/ml. The pH was adjusted to neutral. The broth was then delivered to the NPI Pilot Plant, where it was cooled and filtered. 3899 l of filtered broth were obtained. The HPLC assay gave 19.3 $\mu$g/ml (75.1 g total). The pH was 6.95.

The cold filtered broth was fed simultaneously onto two Dowex 1×2 columns (mesh 50-100) in $HCO_3^-$ cycle (416 l, 75 cm i.d. each, precooled). Flow rate: 34 l/min. on each column.

The loaded columns were washed with cold deionized water and then eluted with cold water saturated with $CO_2$. The elution was monitored by spectrophotometry at 297 min. The fractions were analyzed by HPLC. The spent, wash and forecut contained 7.93 g (10.6%) of thienamycin applied onto the column. 53.2 g (70.8%) were recovered in the rich cut (1408 l). Purity: 7.32%. Further, 1.23 g were found in the tail cut. The overall recovery was 62.4 g (83%), but only the rich cut was used in the next step. The rich cut was concentrated by reverse osmosis to 11.25 l. The final concentration was 4017 mg/l corresponding to 45.2 g total (85% yield on the volume reduction).

The concentrate was loaded onto a Dowex 1×2 column in the Cl$^-$ cycle 83.3 l, 35 cm i.d., washed with pyrogen-free water and precooled). The column was eluted with pyrogen-free water at a flow rate of approximately 2 l/min. After 60.6 l of forecut. 8 l samples were collected and assayed by HPLC. Based on the assays, el. Nos. 5-13 were combined. The composite contained 31.7 g thienamycin in 72 l total solution. The procedure provided the product in 70.2% yield and 41.7% purity. Additional 8.9 g (19.6%) of thienamycin were recovered in the fore and tailcut. However, the purity was below 20% in those fractions.

The rich cut was concentrated by reverse osmosis from 441 mg/l to 4159 mg/l in 97.1% yield. At the same time the purity increased to 48.2%. The 7.40 l of concentrate contained 30.77 g, that were taken to the last isolation step.

The concentrate obtained above was loaded onto an XAD-2 column (83.3 l, 35 cm i.d., mesh 20-50) which was previously washed with 60% aq. acetone and subsequently with cold pyrogen-free water. The column was eluted with cold pyrogen-free water at a flow rate of about 2 l/min. After a fraction of 79.5 l, 12 l cuts were collected and analyzed by HPLC. Based on the titer and purity assays, el. Nos. 4-12 were combined. The 108 l sample contained 22.7 g thienamycin corresponding to 73.8% yield in the XAD-2 step. Additionally, 3.99 g thienamycin (corres. to 12.9%) recovered by combining el. Nos. 3, 13, and 14. Both composite samples were concentrated by reverse osmosis in yields of 85.7% and 72.9%, respectively. The samples have been freeze-dried. The thienamycin content of the products were as follows: primary, 90.8%; secondary, 65.7%.

A total amount of 22.4 q thienamycin was obtained, corresponding to an overall yield of 29.8%.

All the assays were carried out by HPLC. The temperature was kept below 10° C. throughout the whole process. A pH range of 6-7 was maintained for thienamycin solutions.

What is claimed is:

1. In the process for recovering the antibiotic thienamycin from fermentation broths or from solutions containing said antibiotic by purification through column chromatography, the improvement comprising passing the broth or solution, cold, at a pH of from about 6.95 to about 8, through an anion exchange resin of the cross-linked polystyrene-triethylammonium type in the $HCO_3^-$ cycle, followed by elution with a cold aqueous solution of $CO_2$.

2. The process of claim 1 in which the collected combined active fractions recovered from the elution step with $CO_2$ are passed through a column packed with an anion exchange resin of the cross-linked polystyrene-triethylammonium type on the Cl$^-$ cycle, followed by elution with water, then passing the collected combined active fractions into a column packed with a cross-linked polystyrene type resin and eluting with water, then collecting the combined action fractions.

* * * * *